United States Patent [19]

Hesselgren

[11] 4,171,226
[45] Oct. 16, 1979

[54] METHOD OF DESTROYING INFECTIOUS MATERIAL OF DISPOSABLE TYPE

[76] Inventor: Sven-Gunnar Hesselgren, Angsholmen, Drottningholm, Sweden

[21] Appl. No.: 811,435

[22] Filed: Jun. 29, 1977

Related U.S. Application Data

[63] Continuation of Ser. No. 601,632, Aug. 4, 1975, abandoned, which is a continuation-in-part of Ser. No. 333,797, Feb. 20, 1973, abandoned.

[30] Foreign Application Priority Data

Mar. 9, 1972 [SE] Sweden .................................. 2973/72

[51] Int. Cl.² ............................................. C04B 11/00
[52] U.S. Cl. ............................ 106/15.05; 106/18.35; 106/89; 106/109
[58] Field of Search .................. 106/89, 97, 109, 15 R

[56] References Cited

U.S. PATENT DOCUMENTS 3,837,872  9/1974  Conner .................................. 106/74

*Primary Examiner*—Lorenzo B. Hayes

[57] ABSTRACT

The invention relates to a method for destroying infectious material of disposable type, especially medical articles. Such articles are after use immersed in a composition which combined with water or some other solvent results in a solid viscous or sticky compound, which cannot be removed from the material without this becoming destroyed and unfit for further use.

1 Claim, No Drawings

METHOD OF DESTROYING INFECTIOUS MATERIAL OF DISPOSABLE TYPE

This is a continuation application of Ser. No. 601,632, filed Aug. 4, 1975, which is a Continuation-in-part application of Ser. No. 333,797, filed Feb. 20, 1973, both now abandoned.

BACKGROUND OF THE INVENTION

This invention relates a method for destroying infectious materials of a disposable type, especially medical and/or dental articles.

Generally, all waste materials or products involve risks of varying types and magnitude from the viewpoint of general hygiene, professional hygiene and environmental hygiene. In this respect, however, waste products from medical and dental establishments present particularly serious problems because of the risk of spreading infection. Consequently, governmental health and sanitation regulations normally set forth procedural requirements for treatment, handling and disposal of such kinds of waste products.

Generally, such waste products include contaminated objects or paraphernalia, such as disposable hypodermic syringes sharp and pointed waste products; for example, scalpels, hypodermic needles, suturing needles, cannulae, root canal files, glass splinters and the like, as well as biological material, such as bacteriological substrate with growth from the teeth and the oral cavity.

In the medical and dental fields, the disposition of risk waste products such as tampons, swabs, and disposable instruments is a particularly recurring problem. This is especially true when such materials have been utilized in treating patients with hepatitis or other infectious diseases. Furthermore, in regard to hypodermic needles and syringes, particularly, there are explicit hospital and clinic regulations for their destruction since such items are especially sought after by drug addicts. According to present regulations, therefore disposable hypodermic needles and syringes which have been used are destroyed either by machine or manually, the needle being cut to pieces with a pair of tongs or the like. This procedure is, however, complicated and time consuming and also involves an infection risk to the medical personnel who might receive skin scratches while handling these articles. Moreover, even when special machinery is employed to destroy such articles, there are hygienic inconveniences and risks since the apparatus must be cleaned from time to time and may contain highly infectious material after treatment of seriously infected patients. There is a need, therefore, for a method for disposing of such infectious waste products. The present invention fulfills this need.

BRIEF STATEMENT OF THE INVENTION

In accordance with the invention, there is provided a method of destroying medical articles or products after their initial use comprising the steps of immersing the articles directly into a liquid composition which is a mixture of a solvent and a microbicidal agent, adding a solidifying component to the composition, solidifying said composition and forming a solid, viscous or sticky mass adhering to the surfaces of said articles and which can not be removed from the articles without said articles being destroyed and unfit for further use.

DESCRIPTION OF PREFERRED EMBODIMENTS

In carrying out the method of this invention, a wide variety of microbicidal agents can be used and which agents are employed in solution form. Generally, such agents include any microbicidal substance or agent which forms an efficient disinfectant solution in water or other suitably convenient solvent. Among such substances those having the ability to liberate chlorine are particularly effective, especially against virus. Moreover, the concentration of different microbicidal agents can vary widely. As a practical matter, however, concentration of agent in the solution is generally in a range of from about 0.1% to about 20%, although it can be higher or lower. The particular concentration can be adjusted according to the degree of pollution of the products to be decontaminated and as well the time of the contact between the products and the disinfectant. Generally, however, as a practical matter, suitable contact time of the products with the disinfectant is in a range of from about 30 minutes to about three hours. The particular time of exposure can be readily determined for a particular degree and kind of pollution. For example, in this regard, substances rich in protein have a restricting action on the antimicrobial effect of the disinfectant agent and consequently, the concentration is generally increased in such a situation.

Illustrative of useful antimicrobial agents is a water solution of 5% chloramine or a 1.2% to 2.4% chlorinated trisodium phosphate and potassium bromide solution sold under the trademark of K644. These particular agents are especially effective for use with hepatitis virus infected material. Beta-propio-lactone (BPL) is active against vegetative organisms and bacteria spores as well as virus. BPL is used in an 0.2–1% water solution. The purest form of BPL (3.5 mg per ml) acts synergetically with ultraviolet light in the destruction of serum hepatitis virus in blood from blood donors. It hydrolyzes completely to non-toxic acid products when heated to above 37° C.

Chlorhexidine in concentrations of 0.1–1% w/v are active against Gram positive and Gram negative organisms. Chlorine compounds such as hypochlorites, organic and inorganic chloramines, such as chloramine-T and Halazone and $NH_2Cl$ and $NHCl_2$, respectively are also useful in the method of this invention. Their effect is considerably increased by the presence of inorganic bromide and they affect bacteria, virus and to a certain extent also bacteria spores. Sodium hypochlorite solution generally should contain 1%–20% free chlorine. Sodium hypochlorite (1%) can be stabilized by the addition of NaCl (16.5%) which also corrodes metals and accelerates solidification of plaster, useful as a solid compound.

A formaldehyde solution is effective against bacteria spores and is in addition suitable for disinfecting instruments and material contaminated by acid-fast bacilli (tbb) fungus and virus. Pormaldehyde solution (formalin) generally contains 34%–38% formaldehyde (w/w). Dilution for use generally should be 2%–20% (v/v) in water of the concentrate.

Glutaraldehyde is a useful dialdehyde having good microbicidal properties including quick sporicidal, virucidal and tuberculocidal effects. A 2% water solution buffered to pH 7.5–8.5 is a solution useful.

Iodine and iodophors are useful and active as microbicides since free iodine combines with the cell proteins.

Usual concentrations for solutions are 1%–5% iodine in combination with NaI of KI. Iodophors generally contain 0.75–1.6% iodine together with nonionic detergents.

Many types of phenols are also useful such as phenol or carbolic acid, cresols, xylenols, chlorphenols, chloroxylenols, arylphenols, bisphenol and are active primarily against bacteria. Concentrations vary between 0.1 and 10% depending on the preparation and the field of application.

The instruments are immersed into the solution of disinfectant and finally thereto a preferably powdered material is added which makes the mixture solid, viscous or sticky but preferably solid. Such powdered materials include gypsum, cement, plastics and the like and are employed in a sufficient amount to encase the decontaminated products to a degree to make them no further useful. It may also be of a material having adhesive properties such as cold glue powder and the like. Furthermore, mixtures of solidifying components or materials can be employed.

The method is usually carried out in a suitable single container, which is disposed together whith its contents.

In order to more explicitly illustrate the invention, the following example is set forth. It is understood that this example is more illustrative but limitative.

EXAMPLE

A suitable container is partly filled with a suitable microbicide, for example, 5% chloramine in a water solution, and the used infectious objects, for example used hypodermic syringes, are immersed in this solution after use. The needle need not then be touched with the hands or even removed from the syringe, for example. In the case of hypodermic syringes, it is advisable to pull the plunger completely out of the cylinder, after which the parts of the syringe are inserted in the solution. When the container has been almost filled with such infected articles, for example a days requirement or perhaps a longer time in a small medical establishment, gypsum is added to the solution, for example, which gives a solid block of gypsum after a short while, with the parts of the hypodermic syringes embedded therein. The container, which is preferably provided with a lid, can then be disposed of with its solidified contents in the usual manner with general rubbish or the like and be destroyed as a unit. The articles inside the container, which are both decontaminated and firmly fixed in the solid compound, thus do not constitute so-called "risk-waste" which, according to current regulations, must be transported with special precautions. Experiments have shown that it is impossible to break up the gypsum block thus obtained and extract any usable hypodermic needles or parts of hypodermic syringes since the hypodermics are no longer usable after such treatment, the gypsum powder may also have corrosive agent added, for example of the simplest form sodium chloride, so that rust will also attack the enclosed metal parts, for example needles for injection syringes, in a very short time. The addition of sodium chloride also accelerates solidification of the gypsum mixture. Furthermore, due to the pretreatment in microbicidal solution all risks of infection is eliminated.

Numerous advantages of this invention will be readily apparent to those skilled in the art. Moreover, many variations of this invention other than the particular embodiments disclosed herein may be made without departing from the spirit and scope thereof. It is to be understood, therefore, that this invention is not to be limited except as defined in the appended claims.

What is claimed:

1. A method of destroying risk waste, disposable medical, including dental, instruments capable of causing injury after their initial use comprising immersing said instruments directly after use in an aqueous medium containing a microbiocidal agent, in a concentration and for a time sufficient to decontaminate said instruments, said medium being contained in a portable, disposable receptacle, thereafter adding a solidifying component consisting of gypsum to said receptacle to effect the formatiion within said receptacle of a solid mass, embedding and thereby rendering said instruments noninjurious and permanently unfit for further use, and subsequently disposing of said receptacle together with its contents.

* * * * *